US011259777B2

(12) United States Patent
Morikawa et al.

(10) Patent No.: US 11,259,777 B2
(45) Date of Patent: Mar. 1, 2022

(54) ULTRASOUND DIAGNOSIS APPARATUS AND MEDICAL IMAGE PROCESSING METHOD

(71) Applicant: Toshiba Medical Systems Corporation, Otawara (JP)

(72) Inventors: Koichi Morikawa, Nasushiobara (JP); Hironobu Hongou, Otawara (JP); Gen Nagano, Nasushiobara (JP); Kenichi Unayama, Otawara (JP); Satoshi Kamiyama, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 994 days.

(21) Appl. No.: 15/730,826

(22) Filed: Oct. 12, 2017

(65) Prior Publication Data
US 2018/0103926 A1     Apr. 19, 2018

(30) Foreign Application Priority Data

Oct. 17, 2016    (JP) .............................. JP2016-203391
Sep. 13, 2017    (JP) .............................. JP2017-175946

(51) Int. Cl.
*A61B 8/00*          (2006.01)
*A61B 8/08*          (2006.01)
(Continued)

(52) U.S. Cl.
CPC ............ *A61B 8/4477* (2013.01); *A61B 8/461* (2013.01); *A61B 8/467* (2013.01); *A61B 8/5269* (2013.01);
(Continued)

(58) Field of Classification Search
CPC ..................................................... A61B 8/477
See application file for complete search history.

(56) References Cited

U.S. PATENT DOCUMENTS 10,588,603 B2*    3/2020   Yang ...................... A61B 8/465
2006/0173346 A1*  8/2006   Lee ....................... A61B 8/4438
                                                                  600/459
(Continued)

FOREIGN PATENT DOCUMENTS

JP    2000-37383      2/2000
JP    2009-279023     12/2009
(Continued)

OTHER PUBLICATIONS

Office Action dated Jun. 22, 2021 in corresponding Japanese Application No. 2017-175946.

*Primary Examiner* — Bill Thomson
*Assistant Examiner* — Younhee Choi
(74) *Attorney, Agent, or Firm* — Oblon, McClelland, Maier & Neustadt, L.L.P.

(57) ABSTRACT

According to one embodiment, an ultrasound diagnosis apparatus includes a storage and a control unit. The storage stores transmission/reception conditions for a first ultrasound probe among a plurality of ultrasound probes. Upon receipt of a second switching instruction to switch a second ultrasound probe to the first ultrasound probe after a first switching instruction to switch the first ultrasound probe to the second ultrasound probe, the control unit applies the transmission/reception conditions stored in the storage to the first ultrasound probe when the time between the first switching instruction and the second switching instruction is less than a predetermined time.

4 Claims, 14 Drawing Sheets

(51) Int. Cl.
*A61B 8/14* (2006.01)
*G01S 7/52* (2006.01)

(52) U.S. Cl.
CPC .......... *A61B 8/145* (2013.01); *G01S 7/52077* (2013.01); *G01S 7/52098* (2013.01)

(56) References Cited

U.S. PATENT DOCUMENTS

| | | | |
|---|---|---|---|
| 2012/0179037 A1* | 7/2012 | Halmann | A61B 8/54 600/443 |
| 2012/0226161 A1* | 9/2012 | Pelissier | A61B 8/4477 600/443 |
| 2012/0232391 A1* | 9/2012 | Kojima | A61B 8/4477 600/443 |
| 2014/0170620 A1* | 6/2014 | Savitsky | G09B 23/286 434/262 |
| 2016/0106396 A1* | 4/2016 | Jin | A61B 8/4477 600/437 |
| 2016/0262726 A1* | 9/2016 | Yoon | A61B 8/5207 |

FOREIGN PATENT DOCUMENTS

| | | |
|---|---|---|
| JP | 2010-136873 | 6/2010 |
| JP | 2015-123180 | 7/2015 |

\* cited by examiner

FIG. 2

| PROBE ID | TIME | TRANSMISSION/RECEPTION CONDITIONS |
|---|---|---|
| ID1 | T1 | U1 (GAIN, TRANSMISSION POWER, DEPTH...) |
| ... | ... | ... |

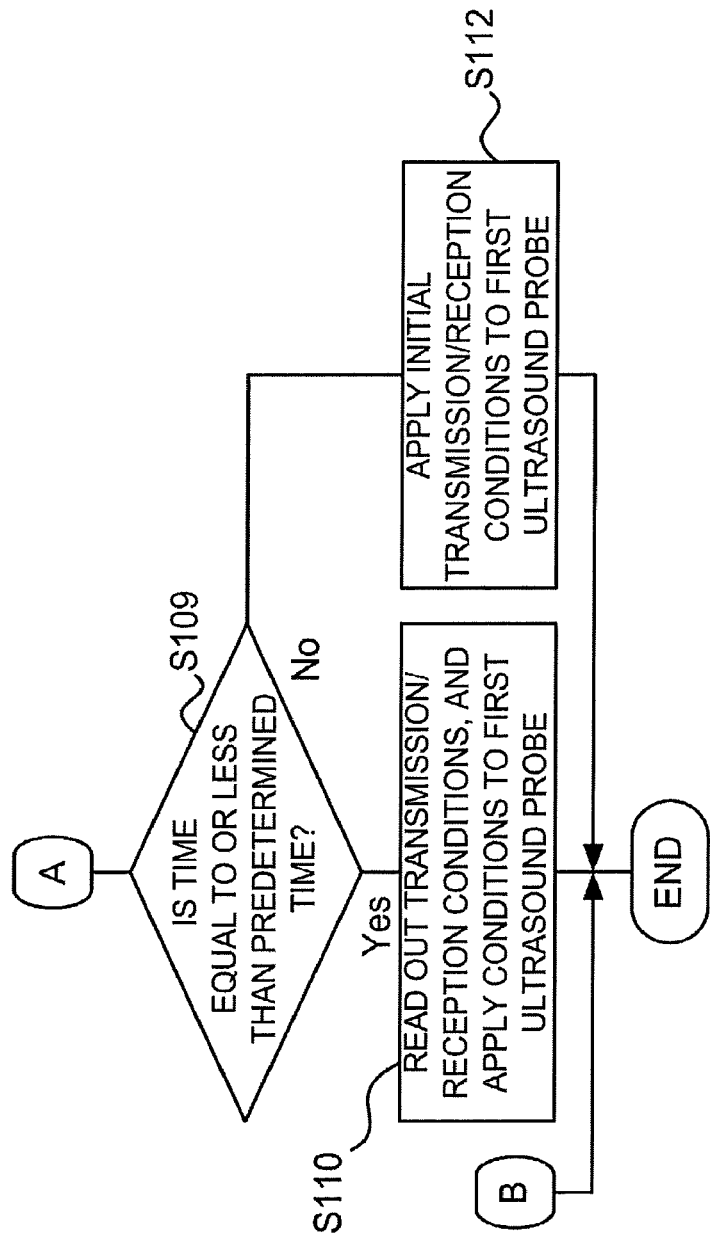

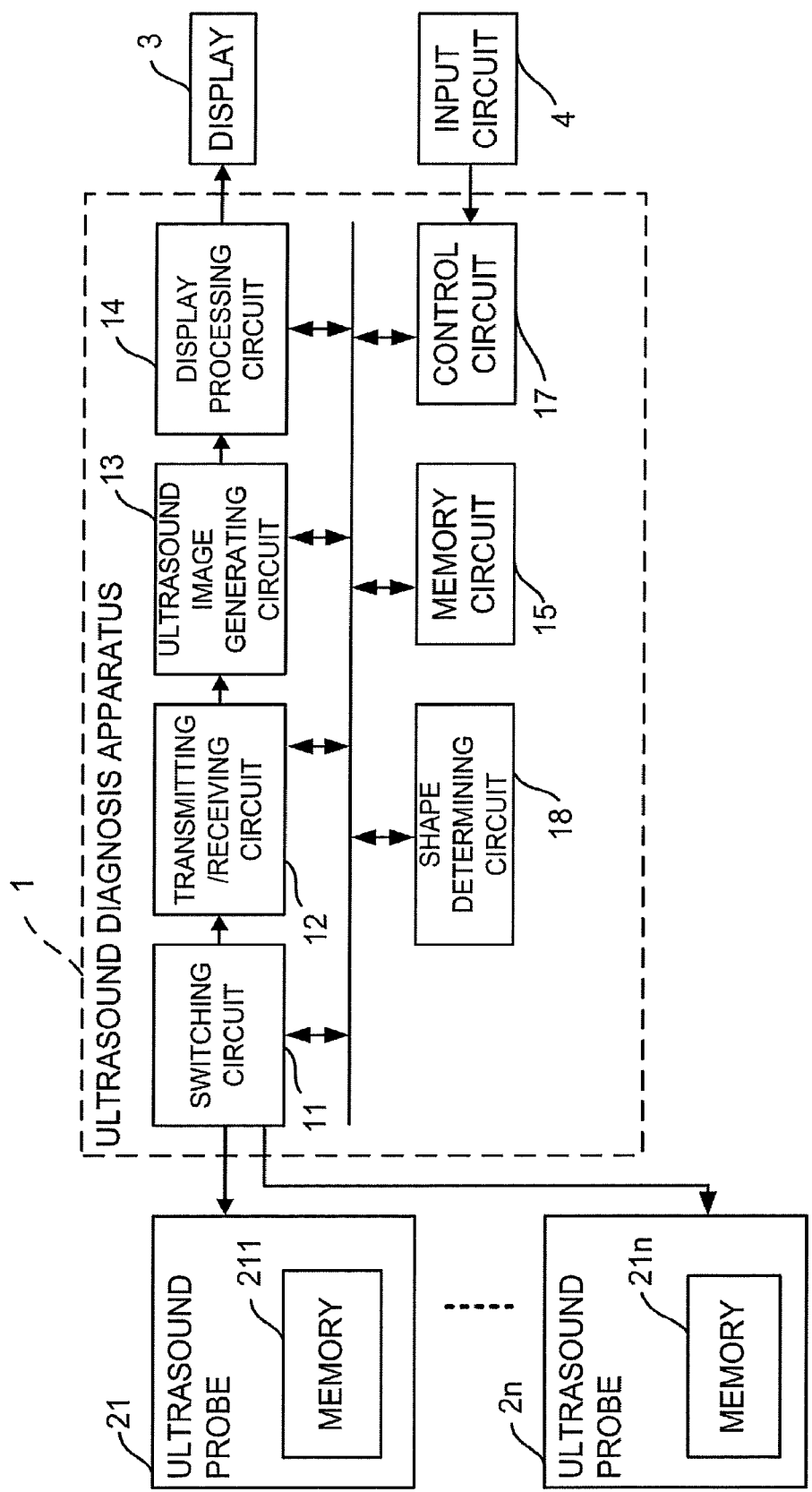

FIG. 5

| PROBE ID | SHAPE INFORMATION | TRANSMISSION/RECEPTION CONDITIONS |
|---|---|---|
| ID1 | F1 | U1 (GAIN, TRANSMISSION POWER, DEPTH...) |
| ... | ... | ... |

FIG. 13

| PROBE ID | DIAGNOSTIC CONDITIONS | TRANSMISSION/RECEPTION CONDITIONS |
|---|---|---|
| ID1 | D1 | U1 (GAIN, TRANSMISSION POWER, DEPTH····) |
| ... | ... | ... |

ULTRASOUND DIAGNOSIS APPARATUS AND MEDICAL IMAGE PROCESSING METHOD

CROSS-REFERENCE TO RELATED APPLICATION(S)

This application is based upon and claims the benefit of priority from Japanese Patent Application No. 2016-203391, filed Oct. 17, 2016; No. 2017-175946, filed Sep. 13, 2017 the entire contents of (all of) which are incorporated herein by reference.

FIELD

Embodiments described herein relate generally to an ultrasound diagnosis apparatus and a computer program product.

BACKGROUND

The ultrasound diagnosis apparatus transmits ultrasound waves to the inside of subject's body through an ultrasound probe and receives reflected waves therefrom to acquire the biological information of the subject. Many types of ultrasound diagnosis apparatuses are configured such that a plurality of ultrasound probes are connected thereto. There are various shapes of ultrasound probes such as linear probes, sector probes, and convex probes. The transmission frequencies are determined with respect to each ultrasound probe. When the ultrasound diagnosis apparatus is used, for example, a plurality of ultrasound probes are connected thereto, and an operator such as a doctor, a technician, or the like selects a desired one of the probes depending on the situation.

In this selection, the operator selects a desired ultrasound probe using an operation device such as a touch command screen (TCS), a button switch, or the like. Similarly, the operator performs ultrasound diagnosis while switching desired ultrasound probes using the operation device. Further, there is a known example in which each ultrasound probe is provided with a contact sensor, and the contact sensor detects that the operator comes in contact with the ultrasound probe.

When performing ultrasound diagnosis while switching ultrasound probes in this manner, the operator may erroneously select an unintended ultrasound probe. For example, depending on the body posture of the subject and the positional relationship of the subject, the operator, and the ultrasound diagnosis apparatus, the operator may use the operation device without watching it carefully and select an unintended ultrasound probe by mistake. In addition, there may be cases that erroneous selection occurs due to simple misoperation as the soft keys or button switches of TCS are narrowly spaced. For example, depending on the examination position, the operator often hold an ultrasound probe on the right hand and extends the left hand to TCS at a distance to operate it. At this time, if the TCS has a flat operation surface without projections and recesses, the operator cannot view the operation surface well. Moreover, since the operator cannot feel the buttons, he/she easily make wrong button operation.

Generally, each time an ultrasound probe is selected, the transmission/reception conditions of the selected ultrasound probe are reset to predetermined initial transmission/reception conditions. Therefore, if an ultrasound probe is erroneously selected and a desired ultrasound probe is selected thereafter, the transmission/reception conditions are reset. In this case, the operator has to set up the transmission/reception conditions, resulting in an increase in the examination time and the operation work.

BRIEF DESCRIPTION OF THE DRAWINGS

FIG. 2 is a schematic diagram illustrating an outline of transmission/reception conditions and time stored in a memory circuit;

FIG. 3B is a flowchart illustrating the operation of the first embodiment;

FIG. 4 is a block diagram illustrating a configuration of an ultrasound diagnosis apparatus according to a second embodiment;

FIG. 5 is a schematic diagram illustrating an outline of transmission/reception conditions and shape information stored in a memory circuit;

FIG. 13 is a schematic diagram illustrating an outline of transmission/reception conditions and diagnostic conditions stored in a memory circuit.

DETAILED DESCRIPTION

Figure 1:
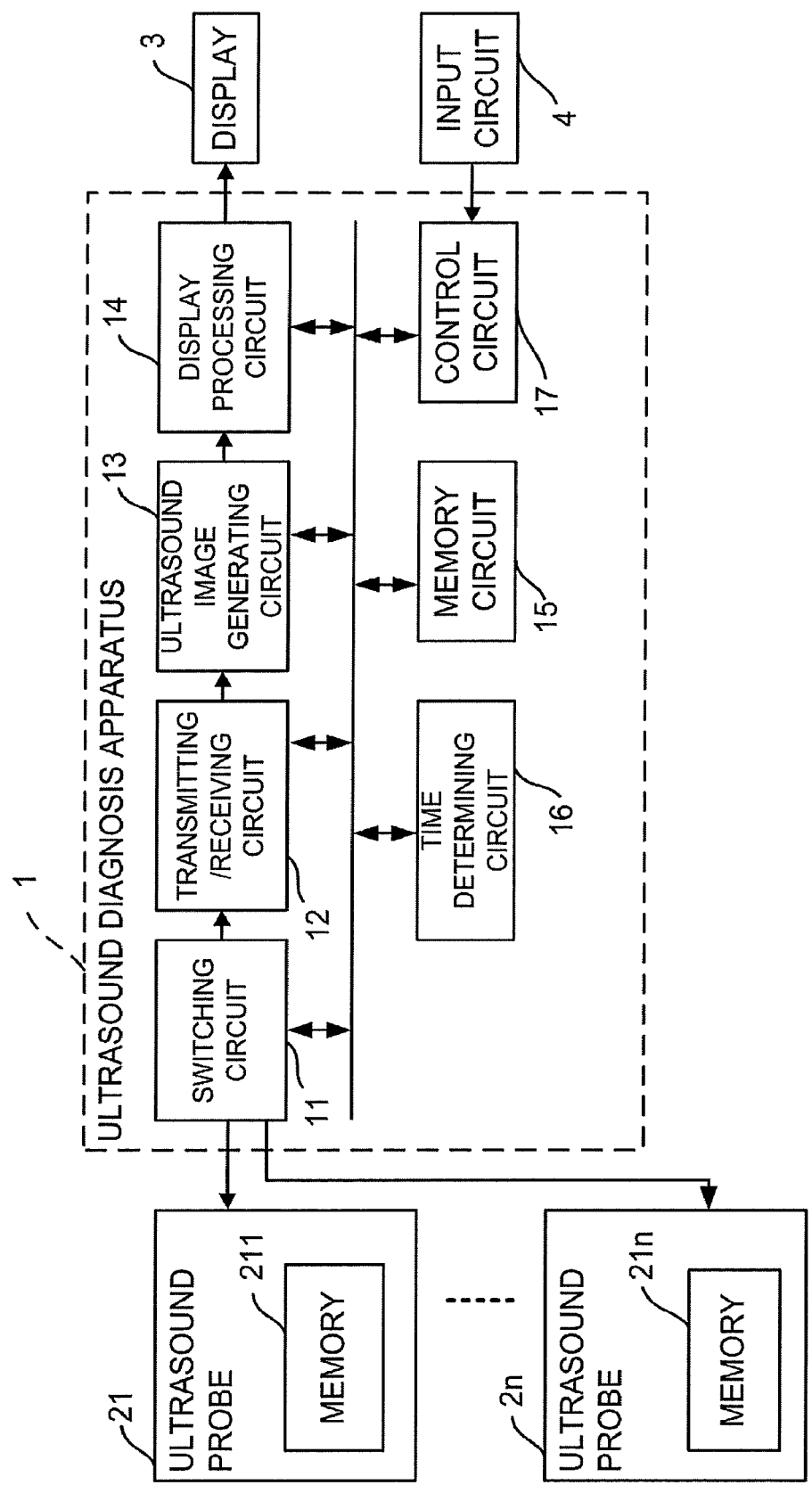
FIG. 1 is a block diagram illustrating a configuration of an ultrasound diagnosis apparatus according to a first embodiment.

In general, according to one embodiment, an ultrasound diagnosis apparatus is configured to be connectable to a plurality of ultrasound probes and capable of switching the ultrasound probes one to another for use. The ultrasound diagnosis apparatus includes a storage, a time determining unit, and a control unit. Upon receipt of an instruction to switch the first ultrasound probe to the second ultrasound probe, the storage stores the transmission/reception conditions of the first ultrasound probe when the instruction is received and the time at which the instruction is received. Thereafter, upon receipt of an instruction to switch the second ultrasound probe to the first ultrasound probe, the time determining unit compares the time from the receipt of the previous instruction with a predetermined time to determine whether the time is not more than or less than the predetermined time. When the time is not more than or less than the predetermined time, the control unit applies the transmission/reception conditions stored in the storage to the first ultrasound probe.

Referring now to the drawings, a description is given of an ultrasound diagnosis apparatus and a computer program product according to embodiments.

First Embodiment

FIG. 1 is a block diagram illustrating a configuration of an ultrasound diagnosis apparatus 1 according to a first embodiment. In this embodiment, the ultrasound diagnosis apparatus 1 includes a switching circuit 11, a transmitting/receiving circuit 12, an ultrasound image generating circuit 13, a display processing circuit 14, a memory circuit 15, a time determining circuit 16, and a control circuit 17. The ultrasound diagnosis apparatus 1 is communicably connected to a plurality of ultrasound probes (21 to 2n), a display 3, and an input circuit 4. The number (n) of ultrasound probes connectable to the ultrasound diagnosis apparatus 1 is predetermined for each model.

Each of the ultrasound probes (21 to 2n) is a one-dimensional array probe having an array of a plurality of ultrasound transducers arranged in the scanning direction, or a two-dimensional array probe having a plurality of ultrasound transducers two-dimensionally arranged. The ultrasound probes (21 to 2n) may be in various shapes such as linear shape, sector shape, convex shape, and the like. The transmission frequency is determined with respect to each ultrasound probe. Shape information indicating the shape of each ultrasound probe, transmission frequency, probe ID, and initial transmission/reception conditions are determined in advance, and stored in a predetermined memory. The location of the memory is appropriately designed. For example, the memory (211 to 21n) may be located in the ultrasound probe.

The switching circuit 11 includes a switch circuit. The switching circuit 11 switches ultrasound probes electrically connected to the transmitting/receiving circuit 12 based on a control signal from the control circuit 17. Thereby, an ultrasound probe selected by the operator is electrically connected to the transmitting/receiving circuit 12. The ultrasound probe that is electrically connected to the transmitting/receiving circuit 12 is referred to as "in-use ultrasound probe". The in-use ultrasound probe transmits and receives ultrasound waves.

The transmitting/receiving circuit 12 includes a pulsar and the like. According to a control signal from the control circuit 17, the transmitting/receiving circuit 12 supplies an electric signal to the in-use ultrasound probe to cause it to transmit ultrasound waves that have been beamformed to a predetermined focal point (subjected to transmission beamforming). Further, the transmitting/receiving circuit 12 receives an echo signal received by the in-use ultrasound probe. The transmitting/receiving circuit 12 converts the analog echo signal into a phased (subjected to reception beamforming) digital data by performing a delay process on the echo signal.

The transmitting/receiving circuit 12 includes, for example, a preamplifier circuit, an A/D converter, a reception delay circuit, and an adder. The preamplifier circuit amplifies the echo signal output from each ultrasound transducer of the in-use ultrasound probe for each reception channel. The A/D converter converts the amplified echo signal into a digital signal. The reception delay circuit gives a delay time necessary to determine the reception directivity to the echo signal converted into the digital signal. The adder adds the echo signal having the delay time. This addition emphasizes the reflection component from a direction corresponding to the reception directivity. The received signal output from the transmitting/receiving circuit 12 is output to the ultrasound image generating circuit 13.

In this manner, conditions of ultrasound waves transmitted and received by the in-use ultrasound probe (transmission/reception conditions) are implemented by the transmitting/receiving circuit 12. Examples of transmission/reception conditions include gain, transmission power, depth, angle of view, and the like. In general, the operator performs ultrasound diagnosis while adjusting transmission/reception conditions using the input circuit 4. The transmission/reception conditions are variously adjusted according to the part and body type of the subject and the diagnostic purpose.

The ultrasound image generating circuit 13 generates an ultrasound image based on the received signal from the transmitting/receiving circuit 12. For example, the ultrasound image generating circuit 13 performs band-pass filtering on the received signal from the transmitting/receiving circuit 12. Thereafter, the ultrasound image generating circuit 13 detects the envelope of the output signal, and performs a compression process on the detected data by logarithmic conversion. The ultrasound image generating circuit 13 converts the received signal subjected to the compression process (ultrasound raster data) into a coordinate system for display (scan conversion), thereby generating an ultrasound image. The ultrasound image generating circuit 13 outputs the ultrasound image to the display processing circuit 14.

The display processing circuit 14 includes a graphics processing unit (GPU) or the like, and displays the ultrasound image on the display 3. The display 3 is formed of a display device such as a liquid crystal display (LCD) or an organic electro-luminescence (EL) display.

The input circuit 4 receives operation by the operator such as a doctor, a technician, or the like, and outputs a signal corresponding to the content of the operation to the control circuit 17. For example, the operator uses the input circuit 4 to select a desired ultrasound probe. Then, a switching instruction is fed from the input circuit 4 to the control circuit 17. The input circuit 4 includes, for example, a trackball, a switch button, a mouse, a keyboard, TCS, a sensitivity time control (STC) slide volume, and the like. The TCS may be provided to a so-called tablet terminal.

In the following, an example is described in which a first switching instruction is provided to switch the in-use ultrasound probe from the first ultrasound probe to the second ultrasound probe, and thereafter a second switching instruction is provided to switch the in-use ultrasound probe from the second ultrasound probe to the first ultrasound probe. The memory circuit 15 is an example of the storage in the claims. The memory circuit 15 stores transmission/reception conditions for a first ultrasound probe among the ultrasound probes (21 to 2n). Upon receipt of an instruction to switch the first ultrasound probe to the second ultrasound probe among the ultrasound probes (21 to 2n), the memory circuit 15 stores the transmission/reception conditions of the first ultrasound probe when the instruction is received and the time at which the instruction is received.

FIG. 2 is a diagram schematically illustrating the transmission/reception conditions and the time stored in the memory circuit 15. Upon receipt a switching instruction, the control circuit 17 outputs transmission/reception conditions U1 at the time T1, i.e., the latest transmission/reception conditions U1 of the first ultrasound probe to the memory circuit 15. The memory circuit 15 stores the transmission/reception conditions U1 received from the control circuit 17 in association with the time T1 at which the switching instruction is received. A general timer function may be used to acquire the time. The control circuit 17 may output the probe ID (ID1) of the first ultrasound probe to the memory circuit 15 together with the transmission/reception conditions U1. In this case, the memory circuit 15 stores the transmission/reception conditions U1 and the time T1 in association with the probe ID (ID1). In this manner, the memory circuit 15 stores the transmission/reception conditions U1 of the in-use ultrasound probe immediately before the receipt of the switching instruction. The memory circuit 15 may store at least the latest transmission/reception conditions and the time (overwrite save). The memory circuit 15 may be configured to accumulate and store transmission/reception conditions and time, and the memory structure related to the storage format may be designed as appropriate.

The time determining circuit 16 is a processor that, when the second switching instruction for switching to the first ultrasound probe is received after the first switching instruction, compares the time from when the first switching instruction is received until the second switching instruction is received with a predetermined time to determine whether the time from the receipt of the first switching instruction is not more than or less than the predetermined time. For example, the predetermined time may be preset as the initial setting of the ultrasound diagnosis apparatus 1, or may be set as appropriate by the operator.

For example, upon receipt of the first switching instruction or the second switching instruction, the control circuit 17 outputs a control signal to the time determining circuit 16. Having received the control signal, the time determining circuit 16 reads out the time stored in the memory circuit 15. With reference to the time read out from the memory circuit 15 and the time of receipt of the control signal from the control circuit 17, the time determining circuit 16 obtains the time from when the first switching instruction is received until the second switching instruction for switching to the first ultrasound probe is received. The time determining circuit 16 compares the obtained time with a predetermined time, and determines whether the time from the receipt of the first switching instruction is not more than or less than the predetermined time. Regarding the relationship between the lengths of both the time periods compared by the time determining circuit 16, the time determining circuit 16 may compare them to determine whether the time from the receipt of the first switching instruction is not more than the predetermined time, or whether the time from the receipt of the first switching instruction is less than the predetermined time. In the following, an example is described in which the time determining circuit 16 determines whether the time from the receipt of the first switching instruction is less than the predetermined time. The time determining circuit 16 outputs determination information indicating the determination result to the control circuit 17.

The control circuit 17 is a processor configured to control the operation of each part of the ultrasound diagnosis apparatus 1. Upon receipt of the second switching instruction for switching to the first ultrasound probe after the first switching instruction for switching from the first ultrasound probe to the second ultrasound probe, when the time between the first switching instruction and the second switching instruction is less than the predetermined time, the control circuit 17 applies the transmission/reception conditions stored in the memory circuit 15 to the first ultrasound probe. For example, when it is determined that the time from the receipt of the first switching instruction is equal to or less than the predetermined time, the control circuit 17 applies the transmission/reception conditions stored in the memory circuit 15 to the first ultrasound probe. When the determination information received from the time determining circuit 16 indicates that the time from the receipt of the first switching instruction is equal to or less than the predetermined time, the control circuit 17 reads out the transmission/reception conditions from the memory circuit 15, and applies the conditions to the first ultrasound probe. At this time, the control circuit 17 outputs a control signal indicating the transmission/reception conditions to the transmitting/receiving circuit 12 to thereby apply the conditions to the first ultrasound probe.

When the determination information received from the time determining circuit 16 indicates that the time from the receipt of the first switching instruction is not equal to or less than the predetermined time, the control circuit 17 applies initial transmission/reception conditions determined in advance to the first ultrasound probe. At this time, the control circuit 17 outputs a control signal corresponding to the initial transmission/reception conditions of the first ultrasound probe to the transmitting/receiving circuit 12 to thereby apply the initial transmission/reception conditions.

Note that from when the first switching instruction is provided for switching the first ultrasound probe to the second ultrasound probe until the second switching instruction is provided for switching the second ultrasound probe to the first ultrasound probe, the control circuit 17 applies the initial transmission/reception conditions to the second ultrasound probe. Then, the control circuit 17 controls (changes, etc.) the transmission/reception conditions according to an operation input or the like from the operator.

Figure 3A:
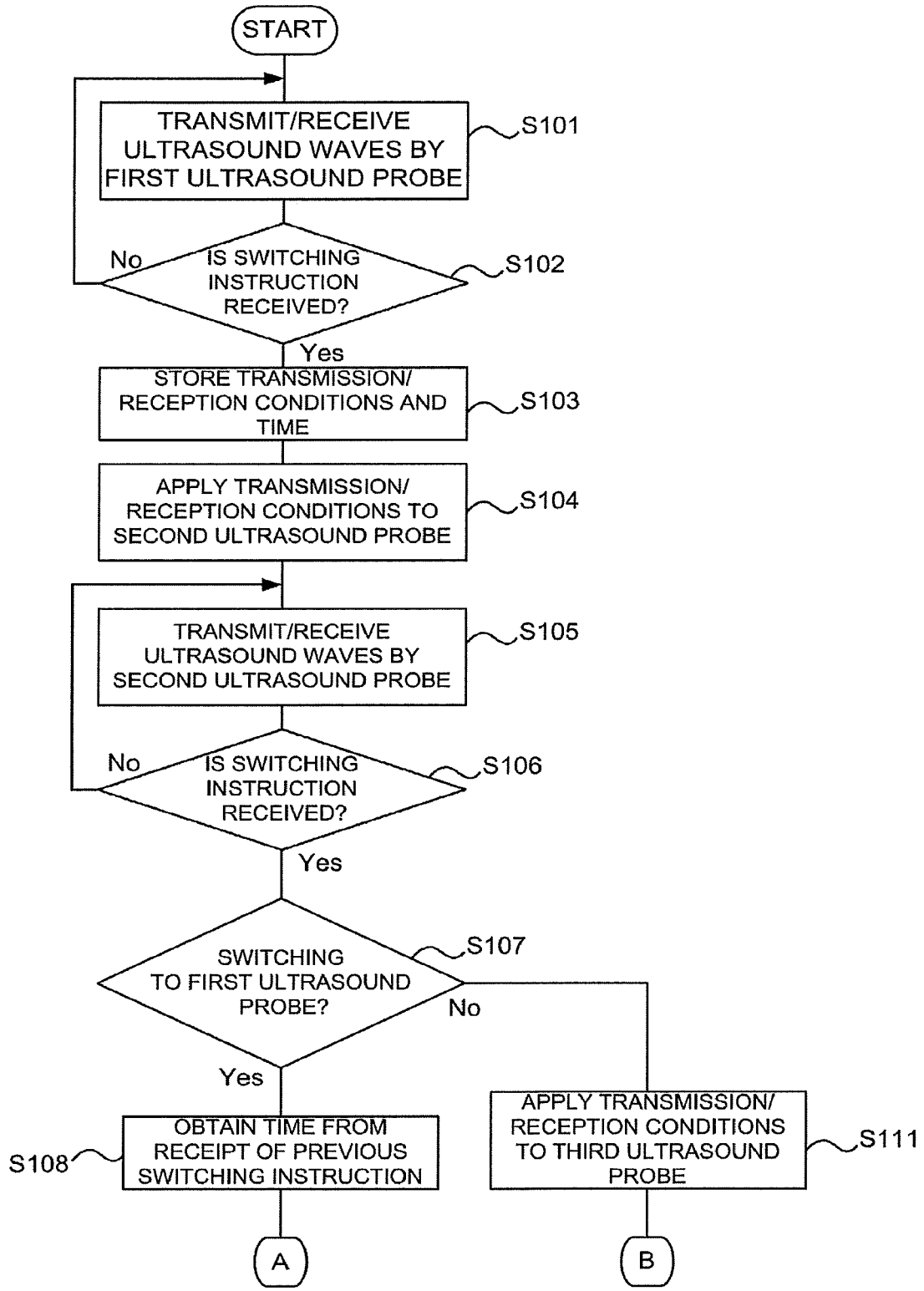
FIG. 3A is a flowchart illustrating the operation of the first embodiment.

FIGS. 3A and 3B are flowcharts illustrating the operation of the first embodiment. For example, the control circuit 17 stores, in advance, a computer program corresponding to the control method of the ultrasound diagnosis apparatus described below and executes it.

Step S101: The first ultrasound probe transmits/receives ultrasound waves to/from the subject based on transmission/reception conditions provided by the control circuit 17 and the transmitting/receiving circuit 12. At this time, the operator can adjust the transmission/reception conditions of the first ultrasound probe using the input circuit 4. In addition, the operator can provide an instruction to switch the in-use ultrasound probe by using the input circuit 4.

Step S102, Step S103: Upon receipt of an instruction to switch the in-use ultrasound probe (Yes in step S102), the control circuit 17 outputs transmission/reception conditions U1 at the time T1, i.e., the latest transmission/reception conditions U1 of the first ultrasound probe to the memory circuit 15. The memory circuit 15 stores the transmission/reception conditions of the first ultrasound probe when the switching instruction is received and the time at which the switching instruction is received. The process of step S101 continues while the instruction to switch the in-use ultrasound probe is not received (No in step S102).

Step S104: The control circuit 17 controls the switching circuit 11 and the transmitting/receiving circuit 12 to switch the in-use ultrasound probe to the second ultrasound probe. At this time, the control circuit 17 applies initial transmission/reception conditions of the second ultrasound probe determined in advance.

Step S105: The second ultrasound probe transmits/receives ultrasound waves to/from the subject based on the transmission/reception conditions provided by the control circuit 17 and the transmitting/receiving circuit 12.

Step S106, Step S107, Step S108: Upon receipt of an instruction to switch the in-use ultrasound probe (Yes in step S106), the control circuit 17 refers to the probe ID indicated by the switching instruction. When the probe ID indicates the first ultrasound probe (Yes in step S107), the control circuit 17 outputs a control signal to the time determining circuit 16. Having received the control signal, the time determining circuit 16 reads out the time stored in the memory circuit 15. With reference to the time read out from the memory circuit 15 and the time of receipt of the control signal from the control circuit 17, the time determining circuit 16 obtains the time from when the previous switching instruction is received until the instruction for switching to the first ultrasound probe is received thereafter. On the other hand, when the instruction to switch the in-use ultrasound probe is not received (No in step S106), the process of step S105 continues.

Step S109: The time determining circuit 16 compares the time obtained with a predetermined time, and determines whether the time from the receipt of the previous switching instruction is equal to or less than the predetermined time. The time determining circuit 16 outputs determination information indicating the determination result to the control circuit 17.

Step S110: When the determination information received from the time determining circuit 16 indicates that the time from the receipt of the previous switching instruction is equal to or less than the predetermined time (Yes in step S109), the control circuit 17 reads out the transmission/reception conditions from the memory circuit 15, and applies the conditions to the first ultrasound probe. Step S110 is an example of the application step in the claims.

Step S111: When the probe ID indicated by the switching instruction is not of the first ultrasound probe (No in step S107), the probe ID indicated by the switching instruction is of an ultrasound probe other than the first ultrasound probe and the second ultrasound probe (referred to as "third ultrasound probe"). At this time, the control circuit 17 switches the in-use ultrasound probe to the third ultrasound probe. Besides, the control circuit 17 outputs a control signal indicating the initial transmission/reception conditions of the third ultrasound probe determined in advance to the transmitting/receiving circuit 12 to thereby apply the conditions to the third ultrasound probe.

Step S112: When the determination information received from the time determining circuit 16 indicates that the time from the receipt of the previous switching instruction is not equal to or less than the predetermined time (No in step S109), the control circuit 17 outputs a control signal indicating the initial transmission/reception conditions of the first ultrasound probe determined in advance to the transmitting/receiving circuit 12 to thereby apply the conditions to the first ultrasound probe.

According to the first embodiment, after the in-use ultrasound probe has been switched, when an operation is performed for switching back the in-use ultrasound probe to the original ultrasound probe within a predetermined time, the latest transmission/reception conditions are used as the transmission/reception conditions of the probe. Thereby, it is possible to prevent the transmission/reception conditions from being reset when, for example, the operator selects again the original ultrasound probe after the in-use ultrasound probe has been switched by an erroneous operation or the like. Thus, the ultrasound diagnosis apparatus of the first embodiment can eliminate the need to set the transmission/reception conditions again, and reduce the examination work and the operation work.

Second Embodiment

FIG. 4 is a block diagram illustrating a configuration of the ultrasound diagnosis apparatus 1 according to a second embodiment. The ultrasound diagnosis apparatus 1 of the second embodiment includes a shape determining circuit 18 in place of the time determining circuit 16 of the first embodiment. In the following, differences from the first embodiment are mainly described.

Upon receipt of an instruction to switch the first ultrasound probe to the second ultrasound probe among the ultrasound probes (21 to 2n), the memory circuit 15 stores the transmission conditions and shape information of the first ultrasound probe. The shape information indicates the shape of the ultrasound probe. Examples of the shape of the ultrasound probe include linear shape, sector shape, convex shape, and the like shape. The shape information of each ultrasound probe can be specified, for example, by reading a memory unique to each of the ultrasound probes (21 to 2n) to which the control circuit 17 is connected.

FIG. 5 is a diagram schematically illustrating the transmission/reception conditions and the shape information stored in the memory circuit 15. Upon receipt a switching instruction, the control circuit 17 outputs the transmission/reception conditions U1 at that time, i.e., the latest transmission/reception conditions U1 of the first ultrasound probe and the shape information F1 of the first ultrasound probe to the memory circuit 15. The memory circuit 15 stores the transmission/reception conditions U1 and the shape information F1 received from the control circuit 17 in association with each other. Incidentally, the control circuit 17 may output the probe ID (ID1) of the first ultrasound probe to the memory circuit 15 together with the transmission/reception conditions U1 and the shape information F1. In this case, the memory circuit 15 stores the transmission/reception conditions U1 and the shape information F1 in association with the probe ID (ID1). In this manner, the memory circuit 15 stores the transmission/reception conditions U1 of the in-use ultrasound probe immediately before the receipt of the switching instruction. The memory circuit 15 may store at least the latest transmission/reception conditions and the time (overwrite save). The memory circuit 15 may be configured to accumulate and store transmission/reception conditions and time, and the memory structure related to the storage format may be designed as appropriate.

The shape determining circuit 18 is a processor configured to determine whether the shape information of the first ultrasound probe and that of the second ultrasound probe correspond to each other. For example, upon receipt of a switching instruction, the control circuit 17 outputs the shape information of the in-use ultrasound probe after the switching instruction (the second ultrasound probe) to the shape determining circuit 18. The shape determining circuit 18 reads out the shape information stored in the memory circuit 15 (the shape information of the first ultrasound probe). The shape determining circuit 18 compares the shape information of the first ultrasound probe with the shape information of the second ultrasound probe to determine whether they correspond to each other.

For example, when the first ultrasound probe is a convex probe, and the second ultrasound probe is also a convex probe, the shape information of the first ultrasound probe and that of the second ultrasound probe both indicate convex shape. In this case, the shape determining circuit 18 determines that the shape information of the first ultrasound probe and that of the second ultrasound probe correspond to each other. In this manner, when the shape information of the first ultrasound probe and that of the second ultrasound probe indicate the same shape, the shape determining circuit 18 determines that the shape information of the first ultrasound probe and that of the second ultrasound probe correspond to each other. On the other hand, when the shape information of the first ultrasound probe and that of the second ultrasound probe indicate different shapes, the shape determining circuit 18 determines that the shape information of the first ultrasound probe and that of the second ultrasound probe do not correspond to each other. The shape determining circuit 18 outputs determination information indicating the determination result to the control circuit 17.

When it is determined that the shape information of the first ultrasound probe and that of the second ultrasound probe correspond to each other, the control circuit 17 applies the transmission/reception conditions stored in the memory circuit 15 to the second ultrasound probe. For example, when the determination information received from the shape determining circuit 18 indicates that the shape information of the first ultrasound probe and that of the second ultrasound probe correspond to each other, the control circuit 17 reads out the transmission/reception conditions from the memory circuit 15, and applies the conditions to the second ultrasound probe. At this time, the control circuit 17 outputs a control signal indicating the transmission/reception conditions to the transmitting/receiving circuit 12 to thereby apply the conditions to the second ultrasound probe.

When the determination information received from the shape determining circuit 18 indicates that the shape information of the first ultrasound probe and that of the second ultrasound probe do not correspond to each other, the control circuit 17 applies initial transmission/reception conditions determined in advance to the second ultrasound probe. At this time, the control circuit 17 outputs a control signal corresponding to the initial transmission/reception conditions of the second ultrasound probe to the transmitting/receiving circuit 12 to thereby apply the initial transmission/reception conditions.

Figure 6:
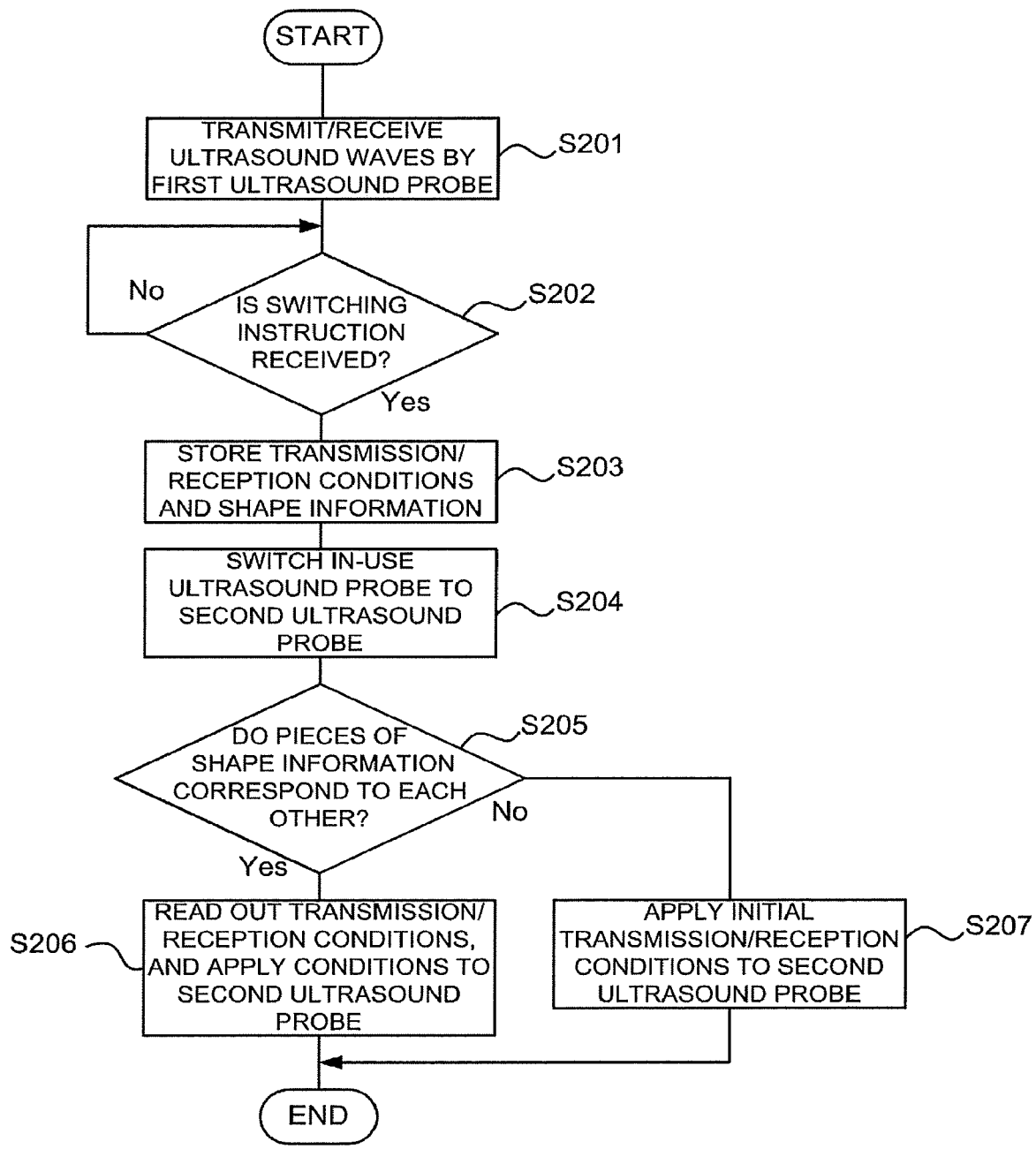
FIG. 6 is a flowchart illustrating the operation of the ultrasound diagnosis apparatus according to the second embodiment.

FIG. 6 is a flowchart illustrating the operation of the second embodiment. For example, the control circuit 17 stores, in advance, a computer program corresponding to the control method of the ultrasound diagnosis apparatus described below and executes it.

Step S201: The first ultrasound probe transmits/receives ultrasound waves to/from the subject based on transmission/reception conditions provided by the control circuit 17 and the transmitting/receiving circuit 12. At this time, the operator can adjust the transmission/reception conditions of the first ultrasound probe using the input circuit 4. In addition, the operator can provide an instruction to switch the in-use ultrasound probe by using the input circuit 4.

Step S202, Step S203: Upon receipt of an instruction to switch the in-use ultrasound probe (Yes in step S202), the control circuit 17 outputs the transmission/reception conditions U1 at that time, i.e., the latest transmission/reception conditions U1 of the first ultrasound probe and the shape information F1 of the first ultrasound probe to the memory circuit 15. The memory circuit 15 stores the transmission/reception conditions U1 and the shape information F1 received from the control circuit 17 in association with each other. The process of step S201 continues while the instruction to switch the in-use ultrasound probe is not received (No in step S202).

Step S204: The control circuit 17 controls the switching circuit 11 to switch the in-use ultrasound probe to the second ultrasound probe.

Step S205: The control circuit 17 outputs the shape information of the in-use ultrasound probe after the switching instruction (the second ultrasound probe) to the shape determining circuit 18. The shape determining circuit 18 reads out the shape information stored in the memory circuit 15 (the shape information of the first ultrasound probe). The shape determining circuit 18 compares the shape information of the first ultrasound probe with the shape information of the second ultrasound probe to determine whether they correspond to each other. The shape determining circuit 18 outputs determination information indicating the determination result to the control circuit 17.

Step S206: When the determination information received from the shape determining circuit 18 indicates that the shape information of the first ultrasound probe and that of the second ultrasound probe correspond to each other (Yes in step S205), the control circuit 17 reads out the transmission/reception conditions from the memory circuit 15, and applies the conditions to the second ultrasound probe.

Step S207: When the determination information received from the shape determining circuit 18 indicates that the shape information of the first ultrasound probe and that of the second ultrasound probe do not correspond to each other (No in step S205), the control circuit 17 outputs a control signal corresponding to the initial transmission/reception conditions of the second ultrasound probe to the transmitting/receiving circuit 12 to thereby apply the initial transmission/reception conditions to the second ultrasound prob.

According to the second embodiment, when the ultrasound probes having the same shape are switched, the transmission/reception conditions can be taken over. For example, in ultrasound diagnosis, the operator may examine while switching ultrasound probes optimal for observing a subject. In this case, ultrasound probes in the same shape with different transmission/reception frequencies may be switched. With the ultrasound diagnosis apparatus of the second embodiment, the transmission/reception conditions, such as the depth and the angle of view, can be taken over when the ultrasound probes are switched one to another. Thereby, it is possible to prevent the transmission/reception conditions from being reset each time the ultrasound probes are switched. Thus, it is possible to eliminate the need to set the transmission/reception conditions again, and reduce the time and operation work related to the switching of the ultrasound probes.

The term "processor" as used herein refers to a circuit such as, for example, a central processing unit (CPU), GPU, an application specific integrated circuit (ASIC), a programmable logic device including a simple programmable logic device (SPLD) and a complex programmable logic device (CPLD), a field programmable gate array (FPGA), or the like. The processor reads programs out of a memory circuit and executes them to thereby realize the functions. The programs need not necessarily be stored in a memory circuit, but may be directly incorporated in the circuit of the processor. In this case, the processor realizes the functions by reading and executing the programs incorporated in the circuit. Each processor of the embodiments need not necessarily be configured as a single circuit. A plurality of independent circuits may be combined to form a single processor for implementing the functions. Besides, a plurality of constituent elements in FIG. 1 may be integrated into one processor to realize the functions.

<First Modification>

In the first embodiment and the second embodiment described above, an example is described in which the operator switches the in-use ultrasound probe by using the input circuit 4; however, the in-use ultrasound probe may be switched by another configuration. For example, each of the ultrasound probes (21 to 2*n*) may be provided with a contact sensor. In one ultrasound probe, the contact sensor may be arranged in a grip portion griped by the operator, or the like.

When the operator grips a desired ultrasound probe, the contact sensor detects the contact of the operator. The contact sensor outputs a detection signal indicating this detection to the control circuit 17. Thereby, the in-use ultrasound probe is switched. In this modification also, it is possible to reduce the time and operation work related to the switching of the ultrasound probes.

<Second Modification>

Figure 7:
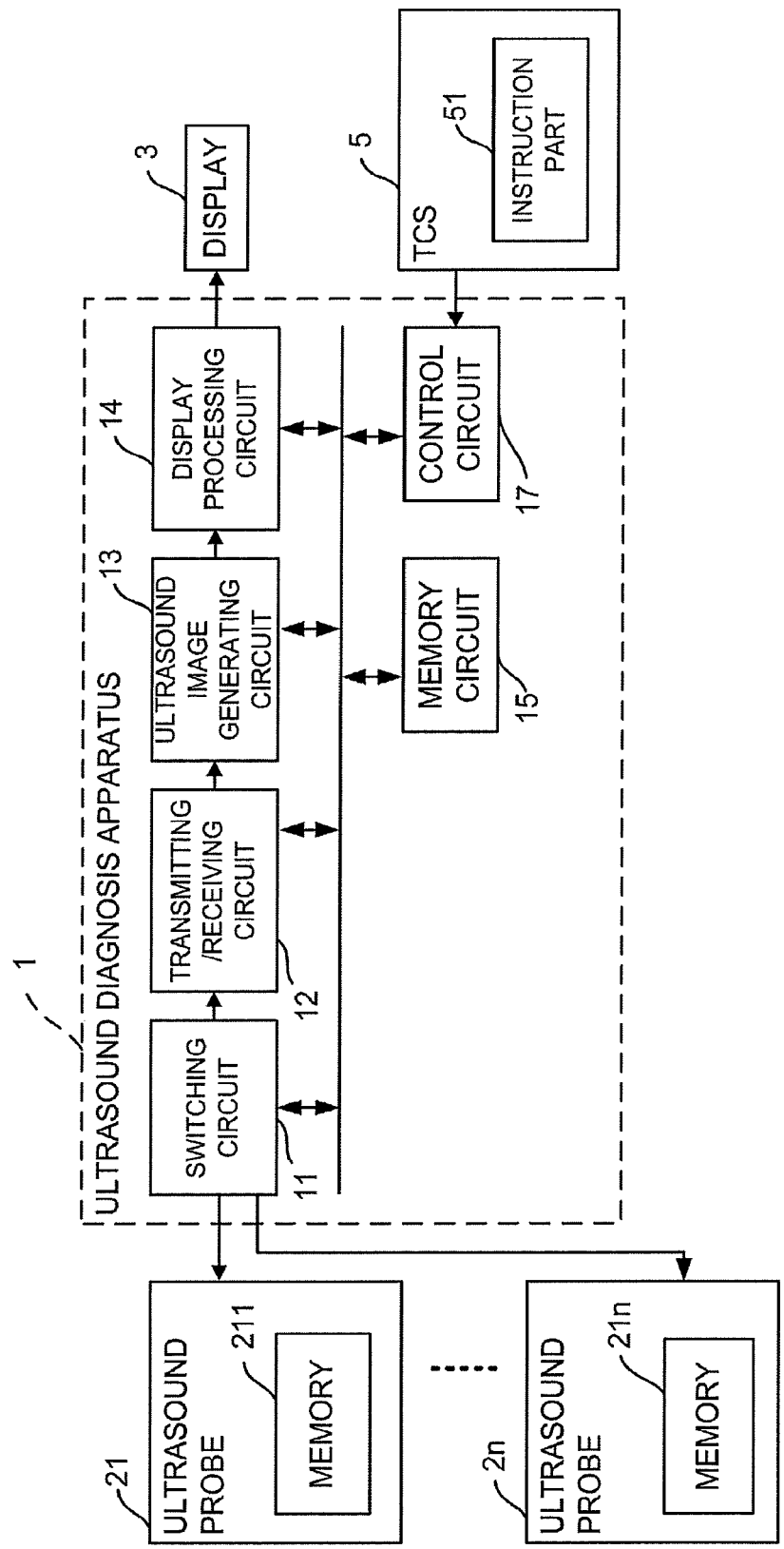
FIG. 7 is a block diagram illustrating a configuration of an ultrasound diagnosis apparatus according to a second modification.

FIG. 7 is a block diagram illustrating a configuration of the ultrasound diagnosis apparatus 1 according to a second modification. The ultrasound diagnosis apparatus 1 of the second modification includes a touch command screen (TCS) 5 and an instruction part 51. In the following, differences from the above embodiments and modification are mainly described.

Figure 8:
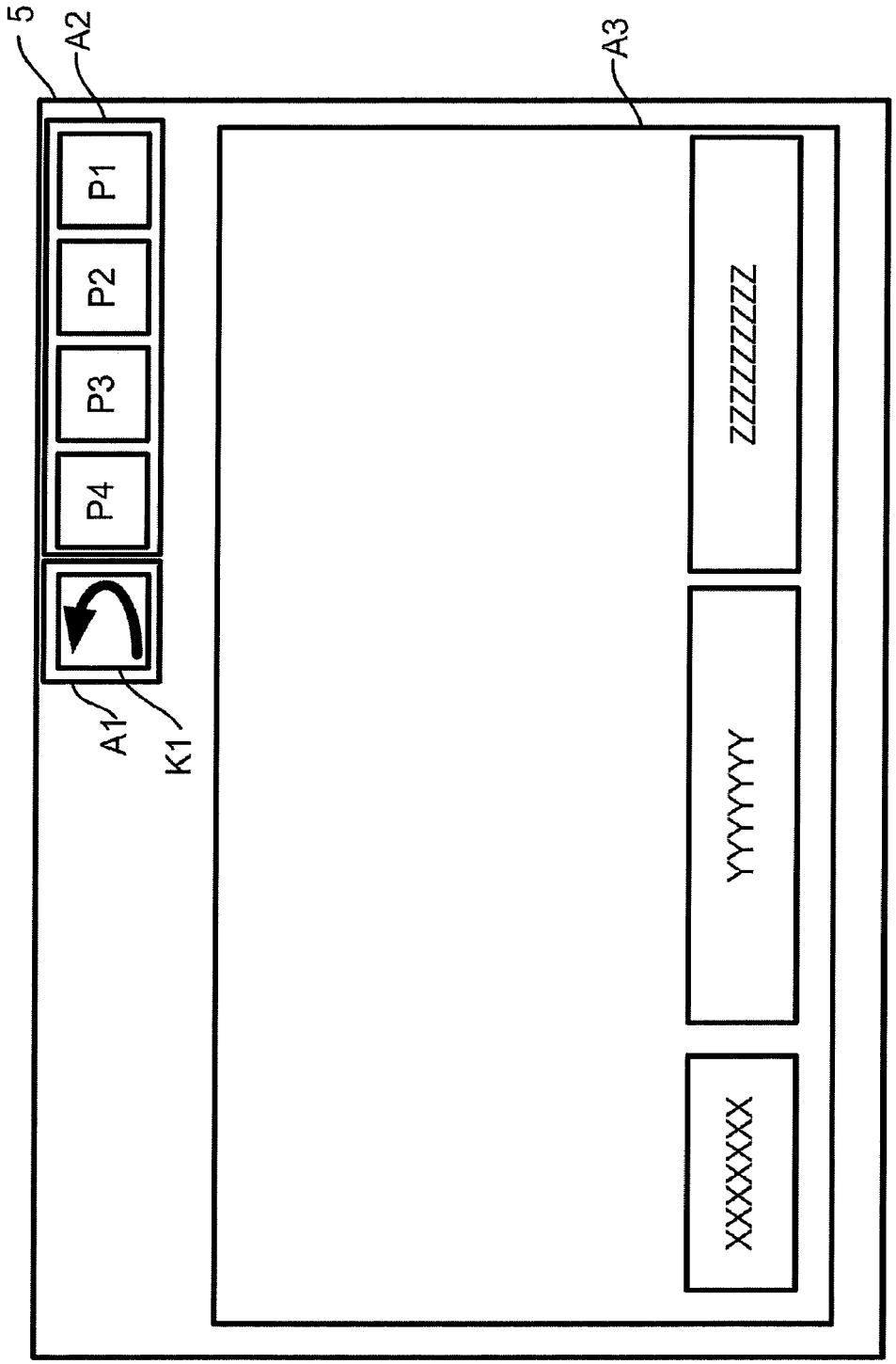
FIG. 8 is a schematic diagram illustrating a display example of a soft key.

The TCS 5 displays various soft keys on the display screen, and outputs a signal corresponding to the soft key touched by the operator to the control circuit 17. FIG. 8 is a diagram schematically illustrating the display screen of the TCS 5 according to the second modification.

For example, the TCS 5 displays a soft key K1 configured to receive an instruction to return to the first ultrasound probe after a first switching instruction to switch the first ultrasound probe to the second ultrasound probe has been received. The soft key K1 is an example of the instruction part in the claims.

In the TCS 5, the soft key K1 is provided in a predetermined area separated from the area for receiving other operation instructions. FIG. 8 illustrates an example in which the soft key K1 is provided in a predetermined area A1 separated from an area A2 for receiving an instruction to switch the in-use ultrasound probe and an area A3 for receiving various operation instructions. Soft keys (P1 to P4) corresponding to ultrasound probes each connected to one of ports of the ultrasound diagnosis apparatus are individually displayed in the area A2. In the example of FIG. 8, four ultrasound probes P1 to P4 are connected to the ultrasound diagnosis apparatus.

When the operator wishes to provide a first switching instruction to switch the in-use ultrasound probe from the first ultrasound probe to the second ultrasound probe while using the first ultrasound probe, he/she touches a soft key corresponding to the second ultrasound probe. At this time, the memory circuit 15 stores transmission/reception conditions of the first ultrasound probe. In this manner, in the memory circuit 15 stores the transmission/reception conditions of the in-use ultrasound probe immediately before the receipt of the first switching instruction. The control circuit 17 switches the in-use ultrasound probe to the second ultrasound probe.

Thereafter, when the operator wishes to switch back the in-use ultrasound probe to the first ultrasound probe, the operator touches the soft key K1. In response to this, the control circuit 17 switches the in-use ultrasound probe to the first ultrasound probe, and applies the transmission/reception conditions stored in the memory circuit 15 to the first ultrasound probe.

Figure 9:
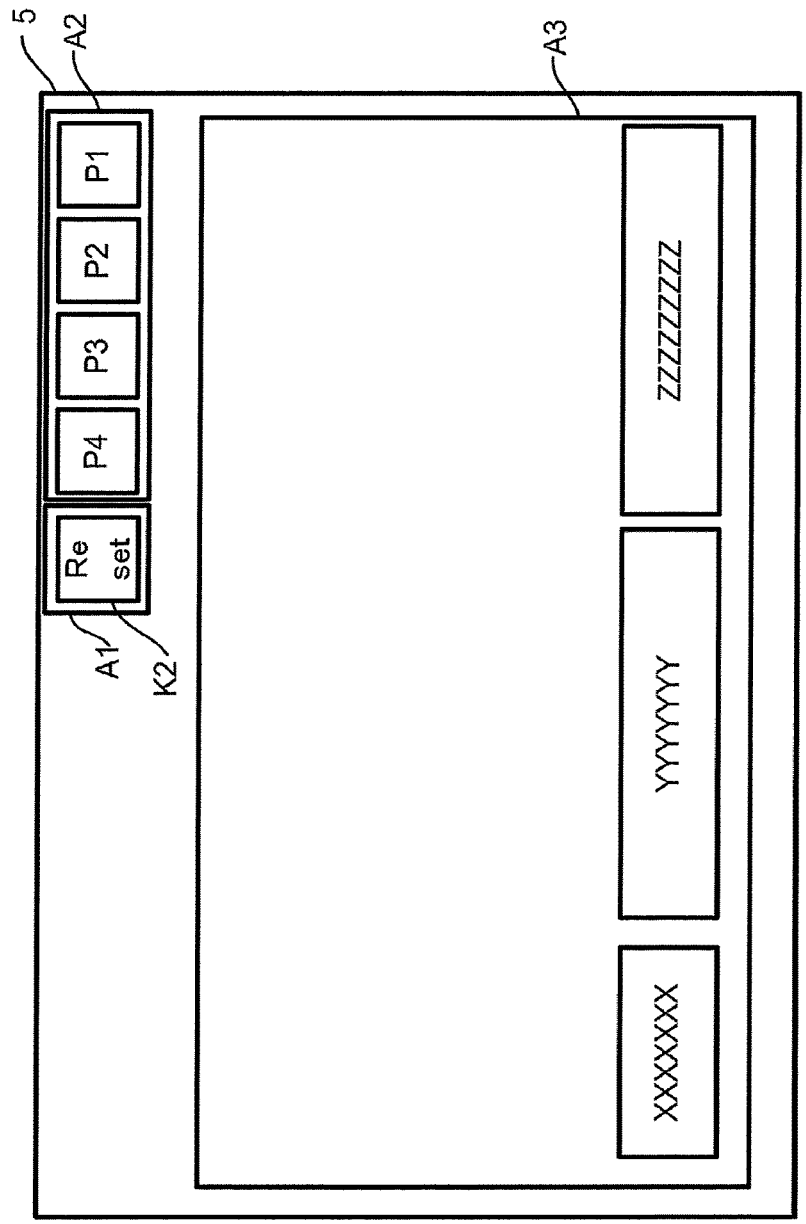
FIG. 9 is a schematic diagram illustrating a display example of the soft key.
Figure 10:
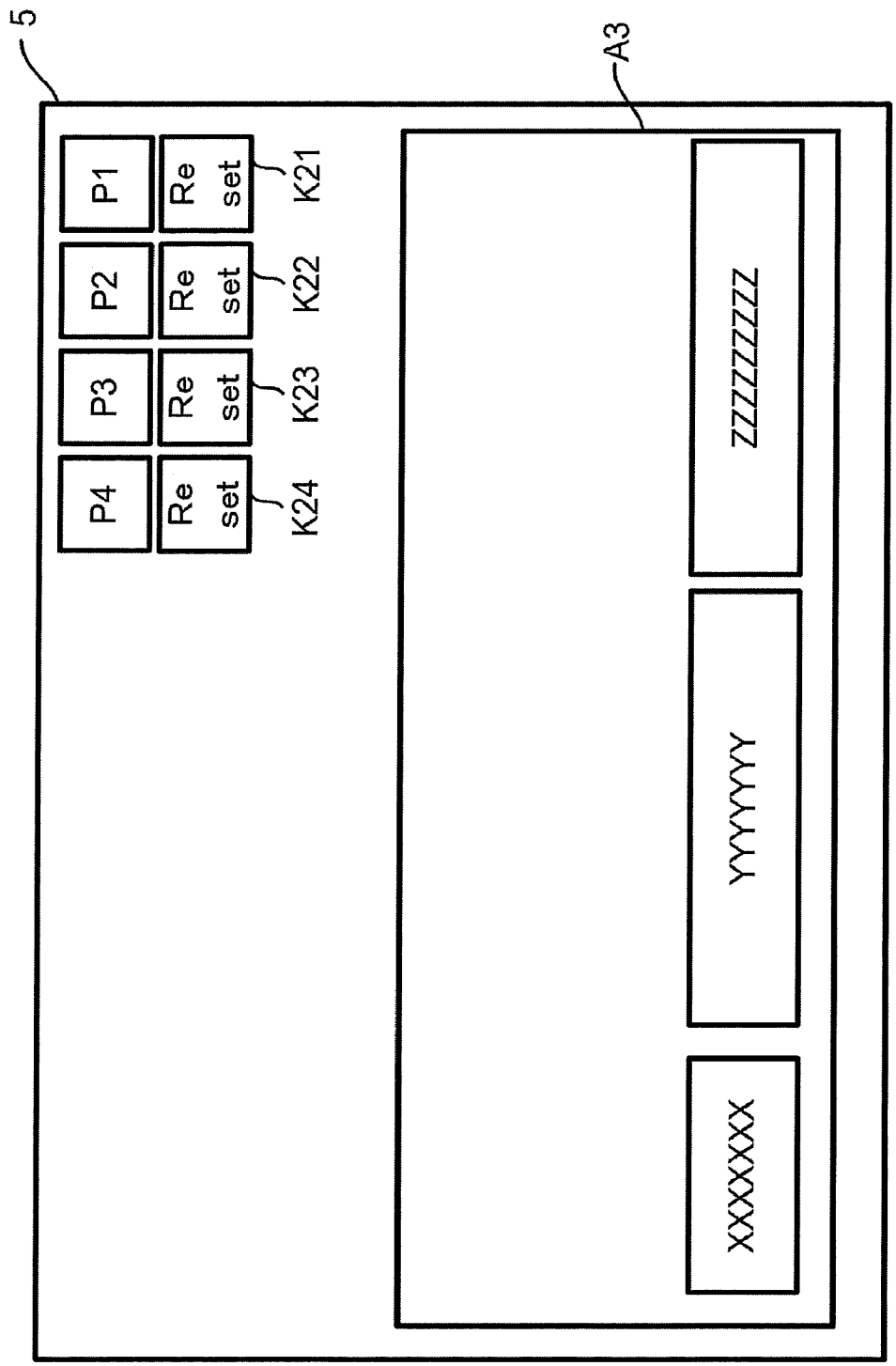
FIG. 10 is a schematic diagram illustrating a display example of the soft key.
Figure 11:
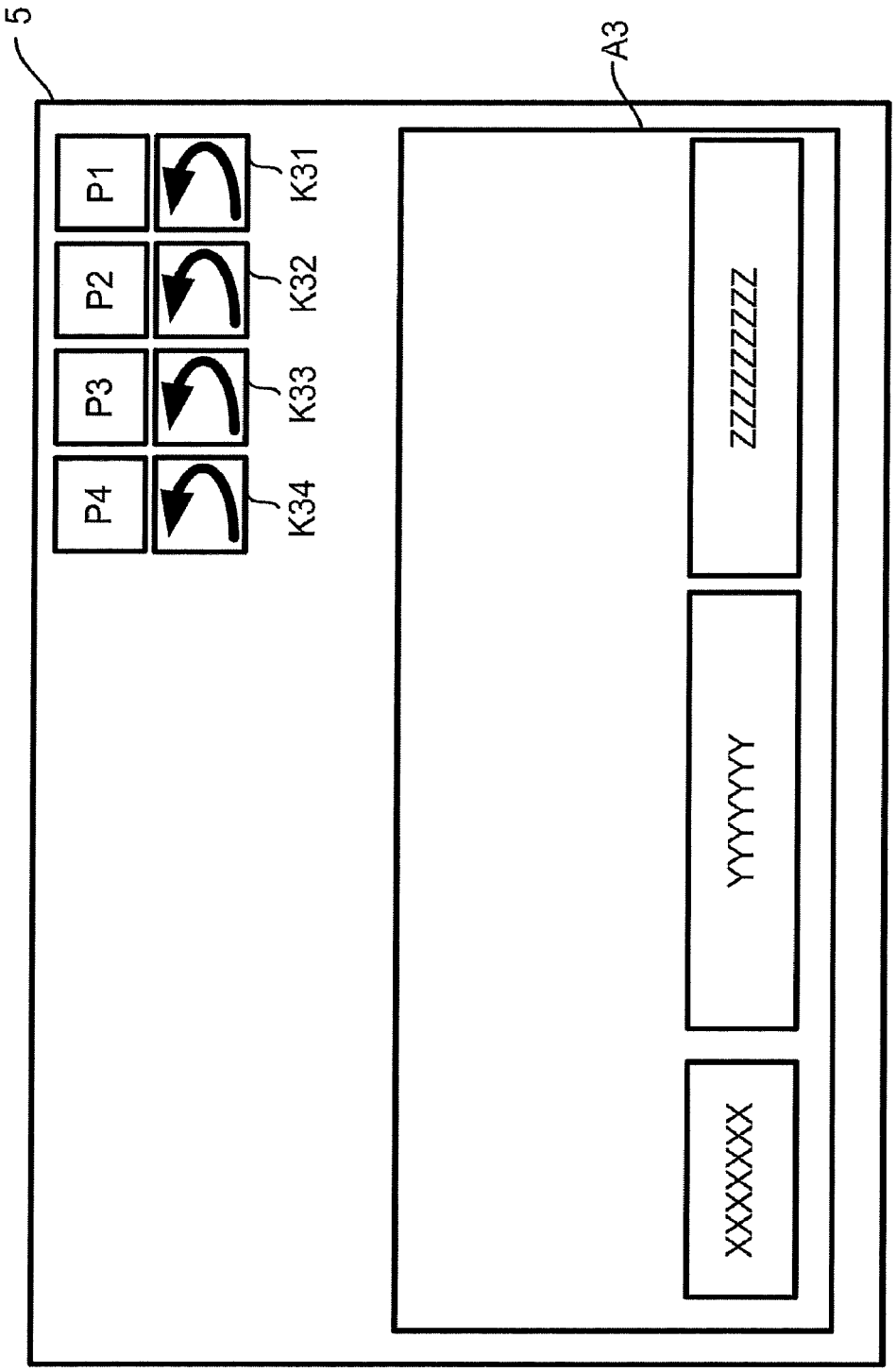
FIG. 11 is a schematic diagram illustrating a display example of the soft key.

FIGS. 9 to 11 are schematic diagrams illustrating other display examples of various soft keys. In the example of FIG. 9, soft keys (P1 to P4) correspond to an example of the instruction part 51. When the operator touches one of the soft keys (P1 to P4), the control circuit 17 switches the in-use ultrasound probe to the ultrasound probe corresponding to the soft key touched. At this time, the control circuit 17 reads out the latest transmission/reception conditions of this ultrasound probe from the memory circuit 15, and applies the conditions to the ultrasound probe. When the operator touches the soft key K2, the control circuit 17 applies the transmission/reception conditions to the in-use ultrasound probe when the key is touched.

In FIG. 10, soft keys (P1 to P4) correspond to an example of the instruction part 51. When the operator touches one of the soft keys (P1 to P4), the control circuit 17 switches the in-use ultrasound probe to the ultrasound probe corresponding to the soft key touched. In addition, the control circuit 17 reads out the latest transmission/reception conditions of this ultrasound probe from the memory circuit 15, and applies the conditions to the ultrasound probe.

Further, when the operator touches one of soft keys (K21 to K24), the control circuit 17 switches the in-use ultrasound probe to the ultrasound probe corresponding to the soft key touched. In addition, the control circuit 17 reads out the initial transmission/reception conditions of this ultrasound probe from the memory circuit 15, and applies the conditions to the ultrasound probe (reset instruction).

As illustrated in FIG. 11, the TCS 5 may display soft keys (P1 to P4) for applying the initial transmission/reception conditions, and soft keys (K31 to K34) for applying the latest transmission/reception conditions. In the example of FIG. 11, when the operator touches one of the soft keys (K31 to K34), the control circuit 17 switches the in-use ultrasound probe to the ultrasound probe corresponding to the soft key touched. In addition, the control circuit 17 reads out the latest transmission/reception conditions of this ultrasound probe from the memory circuit 15, and applies the conditions to the ultrasound probe. Further, when the operator touches one of the soft keys (P1 to P4), the control circuit 17 switches the in-use ultrasound probe to the ultrasound probe corresponding to the soft key touched. In addition, the control circuit 17 reads out the initial transmission/reception conditions of this ultrasound probe from the memory circuit 15, and applies the conditions to the ultrasound probe.

According to the second modification, after the in-use ultrasound probe has been switched, when an operation is performed for switching back the in-use ultrasound probe to the original ultrasound probe, the latest transmission/reception conditions are used as the transmission/reception conditions of the original ultrasound probe. Thereby, it is possible to prevent the transmission/reception conditions from being reset when, for example, the operator uses again the original ultrasound probe after the in-use ultrasound probe has been switched by an erroneous operation or the like. Further, the soft key F1 for receiving this return instruction is located in an area separated from an area for receiving other various operation instructions. This facilitates the input of the return instruction. Thus, it is possible to eliminate the need to set the transmission/reception conditions again, and reduce the examination work and the operation work.

<Third Modification>

Figure 12:
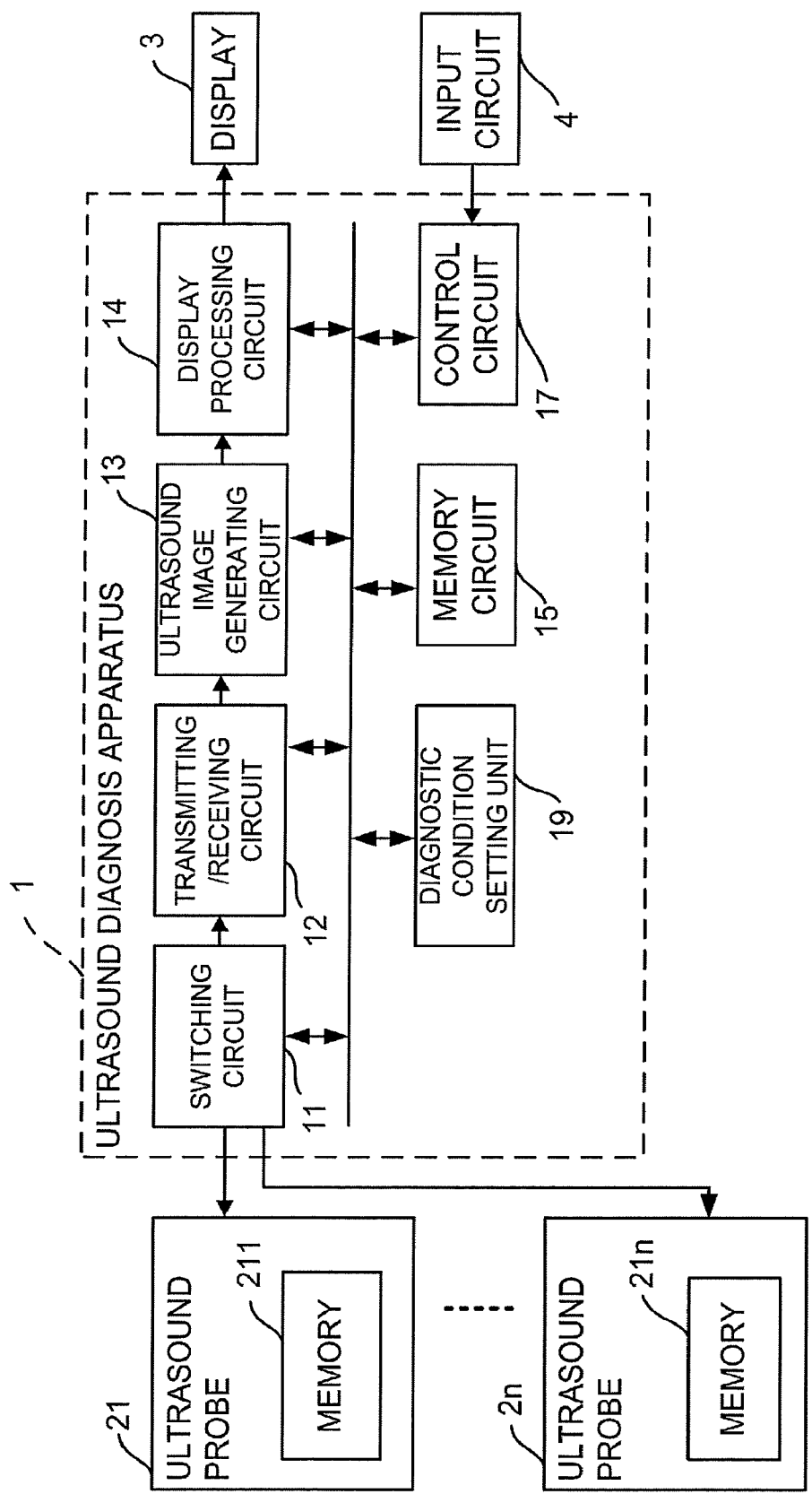
FIG. 12 is a block diagram illustrating a configuration of an ultrasound diagnosis apparatus according to a third modification.

FIG. 12 is a block diagram illustrating a configuration of an ultrasound diagnosis apparatus according to a third modification. The ultrasound diagnosis apparatus 1 of the third modification includes a diagnostic condition setting unit 19. In the following, differences from the above embodiments and modifications are mainly described.

The diagnostic condition setting unit 19 sets diagnostic conditions. Examples of diagnostic conditions include patient ID, site to be diagnosed, and the like. For example, the diagnostic condition setting unit 19 outputs diagnostic condition information indicating a patient ID and a site to be diagnosed to the memory circuit 15 according to an operation input provided by the operator. Besides, the diagnostic condition setting unit 19 sequentially outputs the transmission/reception conditions adjusted by the operator to the memory circuit 15.

The memory circuit 15 stores the adjusted transmission/reception conditions and the diagnostic conditions in association with each other. FIG. 13 is a diagram schematically illustrating the transmission/reception conditions and the diagnostic conditions stored in the memory circuit 15. Upon receipt of a switching instruction, the control circuit 17 stores the latest transmission/reception conditions U1 of the in-use ultrasound probe and the diagnostic conditions D1 in association with each other. The control circuit 17 may output the probe ID (ID1) of the first ultrasound probe to the memory circuit 15 together with the transmission/reception conditions U1 and the diagnostic conditions D1. In this case, the memory circuit 15 stores the transmission/reception conditions U1 and the diagnostic conditions D1 in association with the probe ID (ID1). In this manner, the memory circuit 15 stores the transmission/reception conditions U1 of the in-use ultrasound probe immediately before the receipt of the switching instruction in association with the diagnostic conditions D1 for each probe ID.

Then, the control circuit 17 reads out the transmission/reception conditions associated with the diagnostic conditions and the probe ID of the new in-use ultrasound probe from the memory circuit 15, and applies the conditions to the ultrasound probe. Thereby, the latest transmission/reception conditions for the ultrasound probe and the diagnostic conditions are applied to the in-use ultrasound probe in conjunction with the switching instruction. When the memory circuit 15 does not store the transmission/reception conditions associated with the diagnostic conditions and the probe ID of the new in-use ultrasound probe, the control circuit 17 applies the initial transmission/reception conditions of the ultrasound probe.

For example, even when the same ultrasound probe is used to diagnose the same site, the transmission/reception conditions may vary depending on patients if they have different body types or the like. According to the third modification, the latest transmission/reception conditions of each ultrasound probe corresponding to diagnostic conditions, such as a site to be diagnosed and a patient ID, are applied in conjunction with a switching instruction. Thereby, it is possible to reduce the time and operation work related to the switching of the ultrasound probes.

With the ultrasound diagnosis apparatus and the method of controlling the ultrasound diagnosis apparatus of at least one embodiment described above, it is possible to reduce the time and operation work related to the switching of the ultrasound probes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus configured to be connectable to a plurality of ultrasound probes and capable of switching among the plurality of ultrasound probes for use, the apparatus comprising:

a storage configured to store transmission and/or reception conditions for a first ultrasound probe of the plurality of ultrasound probes; and processing circuitry configured to:

receive selection of the first ultrasound probe to be an in-use ultrasound probe;

receive, while the first ultrasound probe is being selected to be the in-use ultrasound probe, a first switching instruction that instructs the processing circuitry to switch the in-use ultrasound probe from the first ultrasound probe to a second ultrasound probe of the plurality of ultrasound probes;

receive a second switching instruction that instructs the processing circuitry to switch the in-use ultrasound probe from the second ultrasound probe to the first ultrasound probe;

apply the transmission and/or reception conditions stored in the storage for the first ultrasound probe to the first ultrasound probe when the second switching instruction is received within a predetermined time from receipt of the first switching instruction; and apply initial transmission and/or reception conditions determined in advance prior to receiving the second switching instruction to the first ultrasound probe when the second switching instruction is not received within the predetermined time from receipt of the first switching instruction.

2. The ultrasound diagnosis apparatus of claim 1, further comprising a touch command screen configured to receive the first switching instruction and the second switching instruction.

3. The ultrasound diagnosis apparatus of claim 1, wherein the plurality of ultrasound probes include a contact sensor configured to receive the first switching instruction and the second switching instruction.

4. A method of controlling an ultrasound diagnosis apparatus configured to be connectable to a plurality of ultrasound probes and capable of switching among the plurality of ultrasound probes for use, the method comprising:

storing, in a storage, transmission and/or reception conditions for a first ultrasound probe of the plurality of ultrasound probes;

receiving selection of the first ultrasound probe to be an in-use ultrasound probe;

receiving, while the first ultrasound probe is being selected to be the in-use ultrasound probe, a first switching instruction that instructs switching the in-use ultrasound probe from the first ultrasound probe to a second ultrasound probe of the plurality of ultrasound probes;

receiving a second switching instruction that instructs switching the in-use ultrasound probe from the second ultrasound probe to the first ultrasound probe;

applying the transmission and/or reception conditions stored in the storage for the first ultrasound probe to the first ultrasound probe when the second switching instruction is received within a predetermined time from receipt of the first switching instruction; and applying initial transmission and/or reception conditions determined in advance prior to receiving the second switching instruction to the first ultrasound probe when the second switching instruction is not received within the predetermined time from receipt of the first switching instruction.

* * * * *